US00PP36403P2

(12) United States Plant Patent
von Tubeuf

(10) Patent No.: US PP36,403 P2
(45) Date of Patent: Jan. 21, 2025

(54) POINSETTIA PLANT NAMED 'NPCW23402'

(50) Latin Name: *Euphorbia pulcherrima*
Varietal Denomination: NPCW23402

(71) Applicant: KLEMM+SOHN GMBH & CO. KG, Stuttgart (DE)

(72) Inventor: Guido von Tubeuf, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 29 days.

(21) Appl. No.: 18/583,849

(22) Filed: Feb. 21, 2024

(51) Int. Cl.
*A01H 5/02* (2018.01)
*A01H 6/38* (2018.01)

(52) U.S. Cl.
USPC ..... Plt./306
CPC ..... *A01H 6/385* (2018.05)

(58) Field of Classification Search
USPC ..... Plt./306
CPC ..... A01H 6/385; A01H 6/38; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new poinsettia plant particularly distinguished by having pink bicolored bracts, is disclosed.

1 Drawing Sheet

Genus and species: *Euphorbia pulcherrima.*
Variety denomination: 'NPCW23402'.

BACKGROUND OF THE NEW PLANT

The present invention comprises a new and distinct variety of poinsettia, botanically known as *Euphorbia pulcherrima* and hereinafter referred to by the variety name 'NPCW23402'. 'NPCW23402' is a selection in November 2018 from among a set of single plants irradiated from the poinsettia variety 'NPCW18281' (U.S. Plant Pat. No. 31,513).

In May 2019, 'NPCW23402' was first vegetatively propagated by apical cuttings. 'NPCW23402' was found to reproduce true to type in successive generations of asexual propagation via apical cuttings in Stuttgart, Germany.

SUMMARY

The following are the most outstanding and distinguishing characteristics of this new variety when grown under normal horticultural practices in Stuttgart, Germany.

1. Pink bicolored bracts.

DESCRIPTION OF THE PHOTOGRAPH

This new poinsettia plant is illustrated by the accompanying photograph which shows an overall view of the plant. The photograph is of a plant approximately twelve-weeks-old, grown indoors in Stuttgart, Germany in December 2021. The colors shown are as true as can be reasonably obtained by conventional photographic procedures.

DESCRIPTION OF THE NEW VARIETY

The following detailed descriptions set forth the distinctive characteristics of 'NPCW23402'. The data which define these characteristics were collected from asexual reproductions carried out in Stuttgart, Germany. Data was collected on eighteen-week-old plants grown indoors in Stuttgart, Germany under greenhouse conditions in January 2024. Color references are to The R.H.S. Colour Chart of The Royal Horticultural Society of London (R.H.S.), 5$^{th}$ edition (2007).

Classification:
*Family.*—Euphorbiaceae.
*Species.*—*Euphorbia pulcherrima.*
*Common name.*—Poinsettia.
*Variety.*—'NPCW23402'.

Parentage:
*Female.*—Poinsettia variety 'NPCW18281' (U.S. Plant Pat. No. 31,513).

Plant:
*Form.*—Triangular.
*Growth habit.*—Upright.
*Height.*—30 to 32 cm.
*Width.*—28 to 32 cm.
*Average number of inflorescences per plant.*—5.
*Keeping quality.*—Good.
*Time to produce a cutting.*—5 weeks.
*Flowering response time.*—Approximately 50 days.
*Propagation type.*—Apical cuttings.
*Rooting habit and root color.*—Freely branching and white (NN155C).

Lateral branches:
*Color.*—RHS 143A.
*Length.*—27 to 29 cm.
*Internode length.*—1.5 to 3.5 cm.
*Diameter.*—0.5 to 0.8 cm.
*Branching habit.*—Freely branching.
*Number of lateral branches per plant.*—5 to 6.
*Texture.*—Smooth.
*Strength.*—Sturdy.

Leaves:
*Quantity.*—7 to 9 per lateral branch.
*Arrangement.*—Alternate.
*Number of lobes on the leaf blade.*—1 to 2.
*Lobation depth.*—Shallow.
*Depth of the deepest sinus of the leaf blade.*—1 cm.
*Shape.*—Ovate.

*Apex*.—Acute.
*Base*.—Rounded.
*Margin*.—Entire.
*Length*.—10 to 13 cm.
*Width*.—6.0 to 8.0 cm.
*Texture* (*both upper and lower surfaces*).—Upper: Smooth. Lower: Slightly pubescent.
*Vein color*.—Upper surface: RHS 139D. Lower surface: RHS 139D.
*Variegation*.—Absent.
*Venation pattern*.—Reticulate.
*Color*.—Mature foliage: Upper surface: RHS 139A. Lower surface: RHS 137B. Immature foliage: Upper surface: RHS 139A. Lower surface: RHS 137B.
*Leaf petiole*.—Length: 3.0 to 6.0 cm. Diameter: 0.2 to 0.3 cm. Color: Upper (part) surface: RHS 139D. Lower (part) surface: RHS 139D. Texture: Smooth. Strength: Sturdy.
*Transitional leaves*.—Amount: Few. Color: Upper surface: RHS 139B and RHS 37A. Lower surface: RHS 141C and RHS 37A.

Inflorescence:
*Type and habit*.—Cluster of cyathia.
*Quantity per lateral branch*.—1.
*Position relative to foliar plane*.—Above.
*Lastingness of inflorescence on the plant*.—5 to 6 weeks.
*Natural flowering season*.—November and December.
*Diameter*.—22 to 25 cm.
*Height*.—3 to 4 cm.
*Fragrance*.—Absent.

Bracts:
*Number of bracts per inflorescence*.—6 to 8.
*Shape*.—Ovate.
*Apex*.—Acute.
*Base*.—Rounded.
*Margin*.—Mostly entire.
*Size*.—Length: 9 to 14 cm. Width: 5 to 8 cm.
*Texture* (*both upper and lower surfaces*).—Smooth.
*Folding along the main vein*.—Absent.
*Twisting*.—Absent.
*Rugosity between the veins*.—Weak.
*Venation pattern*.—Reticulate.
*Vein color*.—Upper surface: RHS 139D. Lower surface: RHS 139D.
*Bract color*.—Upper surface: RHS 48C and 47C (bicoloured marble pattern). Lower surface: RHS 49B and 48B.
*Bract petiole*.—Length: 1.0 to 2.5 cm. Diameter: 0.2 to 0.3 cm. Color: Upper (part) surface: Closest to RHS 42D. Lower (part) surface: RHS 139D. Texture: Smooth. Strength: Sturdy.

Cyme:
*Diameter*.—1.0 to 2.5 cm.
*Cyathia number*.—4 to 8 per inflorescence.
*Deformation of glands of the cyathium*.—Absent.
*Timing of opening of cyathia*.—First pollen appears in parallel to opening of the nectar cups, stigmas appear 2 weeks later.
*Cyathium*.—Shape: Ovate. Texture (inner and outer surfaces): Smooth. Diameter: 0.2 to 0.4 cm. Length: 0.3 to 0.5 cm. Color: RHS 143B.
*Peduncle*.—Color: RHS 142B. Length: 0.2 to 0-3 cm. Diameter: 0.1 cm. Texture: Smooth. Strength: Sturdy.
*Nectar cups*.—Number: 1 per cyathium. Diameter: 0.1 cm. Length: 0.4 to 0.6 cm. Shape: Lip shaped. Texture: Smooth.

Fruit and seed set: None observed.
Disease and insect resistance: No particular disease or insect resistance observed.

COMPARISON WITH PARENTAL LINE AND KNOWN VARIETY

'NPCW23402' is distinguished from its parent as described in Table 1:

TABLE 1

Comparison with Parental Lines

| Trait or characteristic | Instant variety | Commercial line: 'NPCW18281' |
|---|---|---|
| Bract color | Bicolored RHS 48C and 47C | RHS 48C only |

COMPARISON WITH SIMILAR VARIETY

'NPCW23402' is most similar to the commercial poinsettia plant named 'NPCW16260' (U.S. Plant Pat. No. 29,739). Differences between the two varieties are described in Table 2:

TABLE 2

| Trait or characteristic | Instant variety | Commercial line: 'NPCW16260' |
|---|---|---|
| Bract color | Bicolored RHS 48C and 47C | Marbled RHS 19C and RHS 63A |

I claim:

1. A new and distinct variety of poinsettia plant named 'NPCW23402' as shown and described herein.

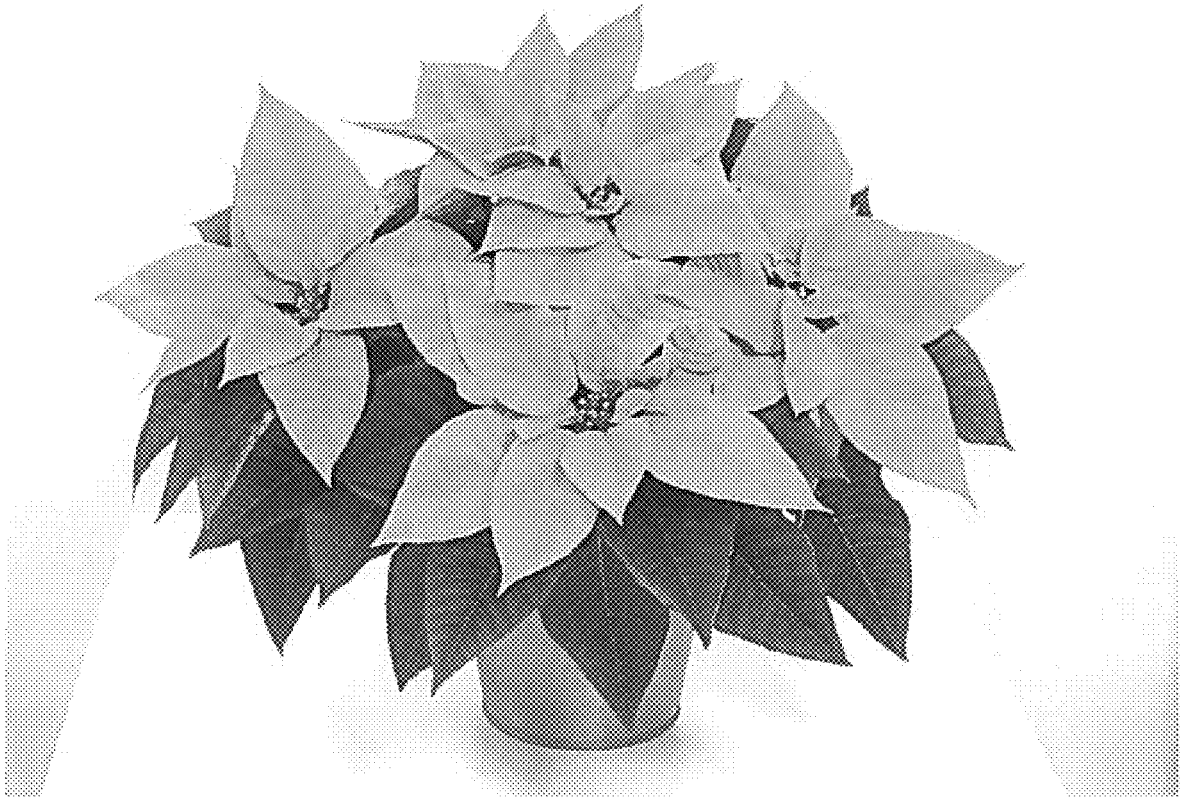

* * * * *